US012575974B2

(12) United States Patent
     Falco et al.

(10) Patent No.: US 12,575,974 B2
(45) Date of Patent: Mar. 17, 2026

(54) SNAP BAND DRESSING DEVICES AND METHODS OF USE

(71) Applicants: Andrew Falco, Chagrin Falls, OH (US); Shyaun Rafii, Charlotesville, VA (US)

(72) Inventors: Andrew Falco, Chagrin Falls, OH (US); Shyaun Rafii, Charlotesville, VA (US)

( * ) Notice: Subject to any disclaimer, the term of this patent is extended or adjusted under 35 U.S.C. 154(b) by 256 days.

(21) Appl. No.: 18/039,092

(22) PCT Filed: Dec. 22, 2021

(86) PCT No.: PCT/US2021/064988
     § 371 (c)(1),
     (2) Date: May 26, 2023

(87) PCT Pub. No.: WO2022/146850
     PCT Pub. Date: Jul. 7, 2022

(65)                Prior Publication Data
     US 2023/0404811 A1      Dec. 21, 2023

Related U.S. Application Data

(60) Provisional application No. 63/132,256, filed on Dec. 30, 2020.

(51) Int. Cl.
     *A61F 13/01*          (2024.01)
(52) U.S. Cl.
     CPC .. *A61F 13/01021* (2024.01); *A61F 13/01008* (2024.01); *A61F 13/01034* (2024.01)
(58) Field of Classification Search
     CPC .......... A61F 13/01021; A61F 13/01008; A61F 13/01034; A61F 13/00051;
                 (Continued)

(56)                References Cited

U.S. PATENT DOCUMENTS 4,297,996 A * 11/1981 Uriza ................. A61B 17/1322
                                                          602/53
     4,728,323 A *  3/1988 Matson ................... A61L 15/46
                                                           451/7
                      (Continued)

FOREIGN PATENT DOCUMENTS

WO    WO-2009128075 A1 * 10/2009 ........... A61K 9/7084

OTHER PUBLICATIONS

International Search report issued Mar. 15, 2022 in international application No. PCT/US2021/064988.
                      (Continued)

*Primary Examiner* — Ophelia A Hawthorne
(74) *Attorney, Agent, or Firm* — Vorys, Sater, Seymour and Pease, LLP; Michael Messinger

(57)                ABSTRACT

Snap band dressing devices and methods are disclosed. The snap band dressing device serves to protect a point of entry from bacteria and other elements found outside the body. For example, the snap band in dressing devices may include a snap band having an elongated open shape and a coiled closed shape, and a layer integral with or coupled to the snap band and configured to elute a fluid to a wound site when the snap band is positioned around the circumferential wound site in the coiled closed shape. Methods are also provided including snapping a snap band in a coiled closed shape about a circumferential wound site and eluting an antimicrobial substance to a wound site when the snap band is positioned around the circumferential wound site in the coiled closed shape.

10 Claims, 6 Drawing Sheets

(58) Field of Classification Search
CPC ............... A61F 13/00063; A61F 13/00; A61F
13/00008; A61F 13/00021; A61F
2013/00089; A61F 13/00085; A61F
13/0233; A61F 13/0243; A61F 13/0246;
A61F 13/01029; A61F 13/01038; A61F
2013/00106; A61F 2013/0028; A61M
35/00; A61K 9/70; A61K 9/7007; A61K
9/7015; A61L 15/00; A61L 26/00
See application file for complete search history.

(56) References Cited

U.S. PATENT DOCUMENTS

| | | | | |
|---|---|---|---|---|
| 5,181,905 | A * | 1/1993 | Flam | A61L 15/56 |
| | | | | 374/161 |
| 6,194,629 | B1 * | 2/2001 | Bernhard | A61F 13/0273 |
| | | | | 602/41 |
| 9,499,852 | B2 * | 11/2016 | Jenkins | C12Q 1/14 |
| 2002/0052570 | A1 * | 5/2002 | Naimer | A61F 13/0273 |
| | | | | 602/53 |
| 2009/0318842 | A1 * | 12/2009 | Kairinos | A61F 13/0226 |
| | | | | 606/59 |
| 2009/0324883 | A1 | 12/2009 | Gray et al. | |
| 2013/0110025 | A1 * | 5/2013 | Donnellan | A61F 13/00063 |
| | | | | 602/46 |
| 2017/0049628 | A1 * | 2/2017 | Stevens | A61F 13/00085 |
| 2018/0360667 | A1 * | 12/2018 | Droche | A61F 13/00063 |
| 2020/0253617 | A1 | 8/2020 | Williams | |

OTHER PUBLICATIONS

Written Opinion issued Mar. 15, 2022 in international application No. PCT/US2021/064988.
"External Fixators", GPC Medical Ltd., Accessed Dec. 28, 2020 (one page).
"External Fixation Device", Medline Plus, Accessed Dec. 28, 2020 (one page).

* cited by examiner

SNAP BAND DRESSING DEVICES AND METHODS OF USE

FIELD

The present disclosure relates to dressings and wound care, and, more particularly to circumferential wound site dressings.

BACKGROUND

External fixators are used to immobilize bones and hold them in a stable position for healing or recovery. Conventional external fixators use a stabilizing frame that can be placed around a bone or area of treatment. The stabilizing frame often requires one or more rings and support rods or struts. Aluminum, titanium, or stainless steel percutaneous pins or wires are inserted into bone that then connect externally to the stabilizing frame. The stabilizing frame and pins provide alignment forces to maintain fracture fragments in proper position during healing or recovery.

External fixators are utilized in circumstances where there is a poor soft tissue envelope or when internal fixation would be contraindicated (such as due to infection, poor bone quality, open wounds, and the like). External fixation pins extrude from the skin and connect to the external stabilizing frame. One of the main complications encountered with the use of external fixation devices are pin site infections. Pin site infections may be caused due to various factors, such as patient-specific physiology, surgical technique, pin design and configuration, post-operative cleaning techniques and frequency, and the like. These infections can endanger the patient, and also pose a significant burden on the healthcare industry, Pin site infections can be mitigated by application of antiseptic materials around the pin site, for example. Applications of these materials can be cumbersome and time consuming and many times fall off due to no real way to secure them or ineffective securing techniques. Moreover, currently available means to apply the antiseptic materials relies on the patient to perform the application and is often forgotten or otherwise ignored due to the difficulties of the application.

DESCRIPTION

In aspects of the present disclosure, snap band pin dressing devices and methods are disclosed. Snap band pin dressing devices and methods are described which overcome the above problems and provides further advantages and features. In various aspects, snap band pin dressing devices and methods protect the pin site and can elute an antiseptic/antimicrobial fluid which may prevent or otherwise minimize microbial (e.g., bacterial) burden and infectious rate while simultaneously maintaining a stable fixation point as a dressing.

It is to be appreciated that while the snap band dressing devices of the present disclosure are described with reference to external fixator pins and/or wires, the snap band dressing devices may be used on any external (percutaneous) circumferential structure entering the skin and requiring a wound dressing, without limitation, such as catheter sites, for example. These percutaneous sites are referred to herein collectively as "circumferential wound sites."

Further aspects, features, and advantages of the invention, as well as the structure and operation of the various embodiments of the invention are described in detail below with reference to accompanying drawings.

BRIEF DESCRIPTION OF THE DRAWINGS

The accompanying drawings, which are incorporated into and constitute a part of this specification, illustrate one or more examples of aspects of the present disclosure and, together with the description of examples herein, serve to explain the principles and implementations of the embodiments. The drawings should not be viewed as exclusive configurations. The subject matter disclosed is capable of considerable modifications, alterations, combinations, and equivalents in form and function, as will occur to those skilled in the art and having the benefit of this disclosure.

DETAILED DESCRIPTION

Figure 1:
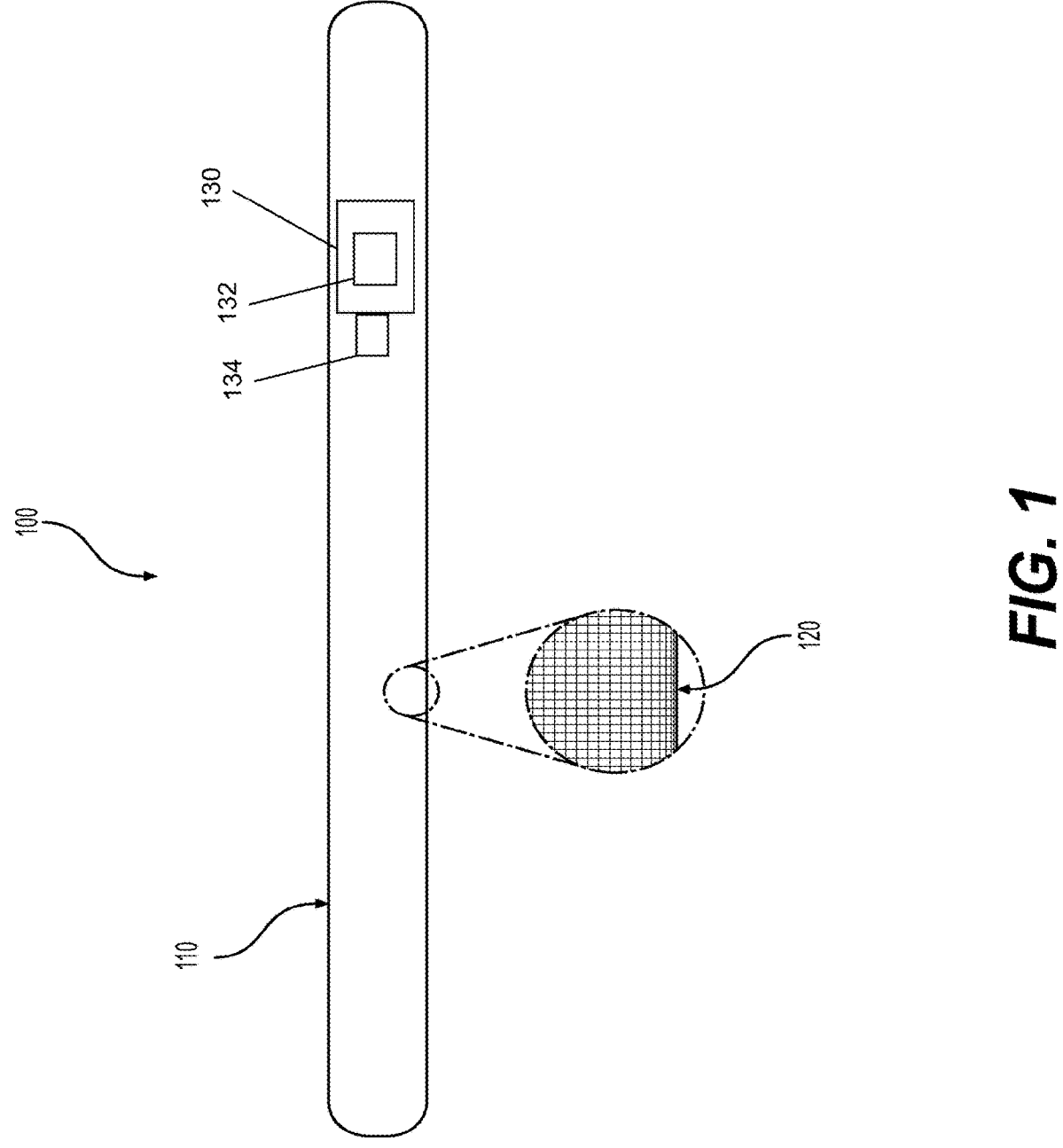
FIG. 1 is a diagram of a snap band dressing device according to one or more aspects of the present disclosure.

In aspects of the present disclosure, snap band dressing devices and methods are disclosed. In one or more aspects, a snap band dressing device couples with a wound dressing material or foam and serves to protect a point of entry from bacteria and other elements found outside the body. For example, external fixation pins may be used to insert percutaneous pins from external to internal and attach to an external stabilizing frame, including but not limited to, providing alignment forces to maintain reduction of fracture fragments and deformity correction.

The following description is illustrative only and is not intended to be in any way limiting. Other aspects will readily suggest themselves to those of ordinary skill in the art having the benefit of this disclosure. Reference will be made in detail to implementations of the examples as illustrated in the accompanying drawings. The same reference indicators will be used to the extent possible throughout the drawings and the following description to refer to the same or like items.

In the description of example embodiments that follows, references to "one aspect", "an aspect", "an example aspect", "certain aspects," and the like, indicate that the aspect described may include a particular feature, structure, or characteristic, but every aspect may not necessarily include the particular feature, structure, or characteristic. Moreover, such phrases are not necessarily referring to the same aspect and such aspects may be combined with other aspects without limitation, unless otherwise stated. When a particular feature, structure, or characteristic is described in connection with a particular aspect, it is submitted that it is within the knowledge of one skilled in the art to effect such feature, structure, or characteristic in connection with other aspects whether or not explicitly described.

As used herein, the term "snap band circumferential wound site dressing device" or simply "snap band dressing device," and grammatical variants thereof, refers to a dressing that is collapsible around a percutaneous circumferential wound site, such as a pin site for an external fixator or a catheter site, and the like, that provides microbial infection protection. The snap band dressing device includes a snap band substrate with a bistable spring having two stable mechanical shapes stabilized by different curvature axes, thus allowing an elongated open structure to roll up into a smaller cylinder. The snap band may be made of any flexible material, such as a flexible polymer (e.g., silicone) or a flexible metal (e.g., stainless steel), with bistable spring capability, and may be otherwise coated or covered chemically or mechanically on one or both faces with layer(s) of material to facilitate comfort and/or adherence (or coating) of an antimicrobial substance or antimicrobial containing material.

As used herein, the term "antimicrobial substance" or simply "antimicrobial," and grammatical variants thereof, refers to any substance that is able to destroy or inhibit the growth of microorganisms, including bacteria, fungus, virus, other pathogens, and the like, and any combination thereof. Examples of suitable antimicrobial substances include, but are not limited to, alcohol, peroxide, chlorhexidine, acetic acid, silver, an iodine (e.g., cadexomer iodine, providone-iodine such as BETADINE®, Avrio Health L.P., Stamford Forum), polyhexamethyl biguanide, sodium hypochlorite, VASHE® (hypochlorous acid) (Byram Healthcare, White Plains, New York), PRONTOSAN® (betaine-polyhexanide) (B. Braun Medical Inc., Melsungen, Germany), other antimicrobial substances, and the like, and any combination thereof. In some aspects, the antimicrobial substance may be directly coated upon the snap band or on a layer surrounding some or all of the snap band. As used herein, the term "coating" (also referred to as a film) refers to partial or complete coating of the snap band, without limitation. In alternative or additional aspects, the antimicrobial substance may be contained within a material.

As used herein, the term "antimicrobial substance containing material," or simply "antimicrobial containing material," and grammatical variants thereof, refers to a biocompatible material comprising or capable of comprising (e.g., receiving) an antimicrobial substance. The material contains or is otherwise fed (e.g., from a cell containment opening) the antimicrobial substance for contact with a circumferential wound site (e.g., pin site wound) or otherwise allows elution of the antimicrobial substance to a circumferential wound site (e.g., pin site wound). For example, the antimicrobial containing material may comprise open cells (e.g., a foam) that receives and holds an antimicrobial substance in place for slow elution over time and while in use. Accordingly, the antimicrobial containing material need not initially contain the antimicrobial substance prior to its deployment to a circumferential wound site. Examples of suitable antimicrobial containing materials include, but are not limited to, biocompatible foam materials, hydrogel materials, hydrocolloid materials, alginate materials, and the like, and any combination thereof. Such materials may be biocompatible natural or synthetic polymers, such as polyurethane, silicone, gelatin, pectin, cellulose (e.g., carboxymethyl-cellulose, gauze (cotton)), guar gum, ADAPTIC™ (knitted cellulose acetate fabric impregnated with a petrolatum emulsion) (KCI USA, Inc., San Antonio, TX), or XEROFORM™ (sterile, non-adherent gauze dressing containing a petrolatum blend with bismuth tribromophenate) (Cardinal Health, Inc., Dublin, Ohio), and the like, and any combination thereof.

As used herein, the term "biocompatible adhesive," and grammatical variants thereof, refers to an adhesive used to adhere the antimicrobial containing material to the snap band substrate directly or to an outer layer of material surrounding at least a portion, including all, of the snap band substrate. Suitable biocompatible adhesives may include, but are not limited to, silicone adhesives, epoxide adhesives, acrylate adhesives (e.g., cyanoacrylate adhesives), and the like, and any combination thereof.

The term "snap band" is used herein to refer to the snap band substrate and any additional layer(s) that do not encompass the antimicrobial substance and/or antimicrobial containing material and, thus, constitute otherwise biocompatible, inert materials with respect to antimicrobial activity.

FIG. 1 shows a snap band dressing device 100 according to one or more aspects of the present disclosure. Snap band dressing device 100 includes a snap band 110 having a bistable spring (not shown) and an antimicrobial coating (e.g., film) 120. Using the bistable spring allows for close approximation of the dressing onto the skin surface as well as the circumferential wound site (e.g., pin site) it surrounds. As illustrated in FIG. 1, in one example, antimicrobial coating 120 may include, but is not limited to, an antimicrobial containing material, such as gauze, provided integral with or coupled to snap band 110.

Figure 2:
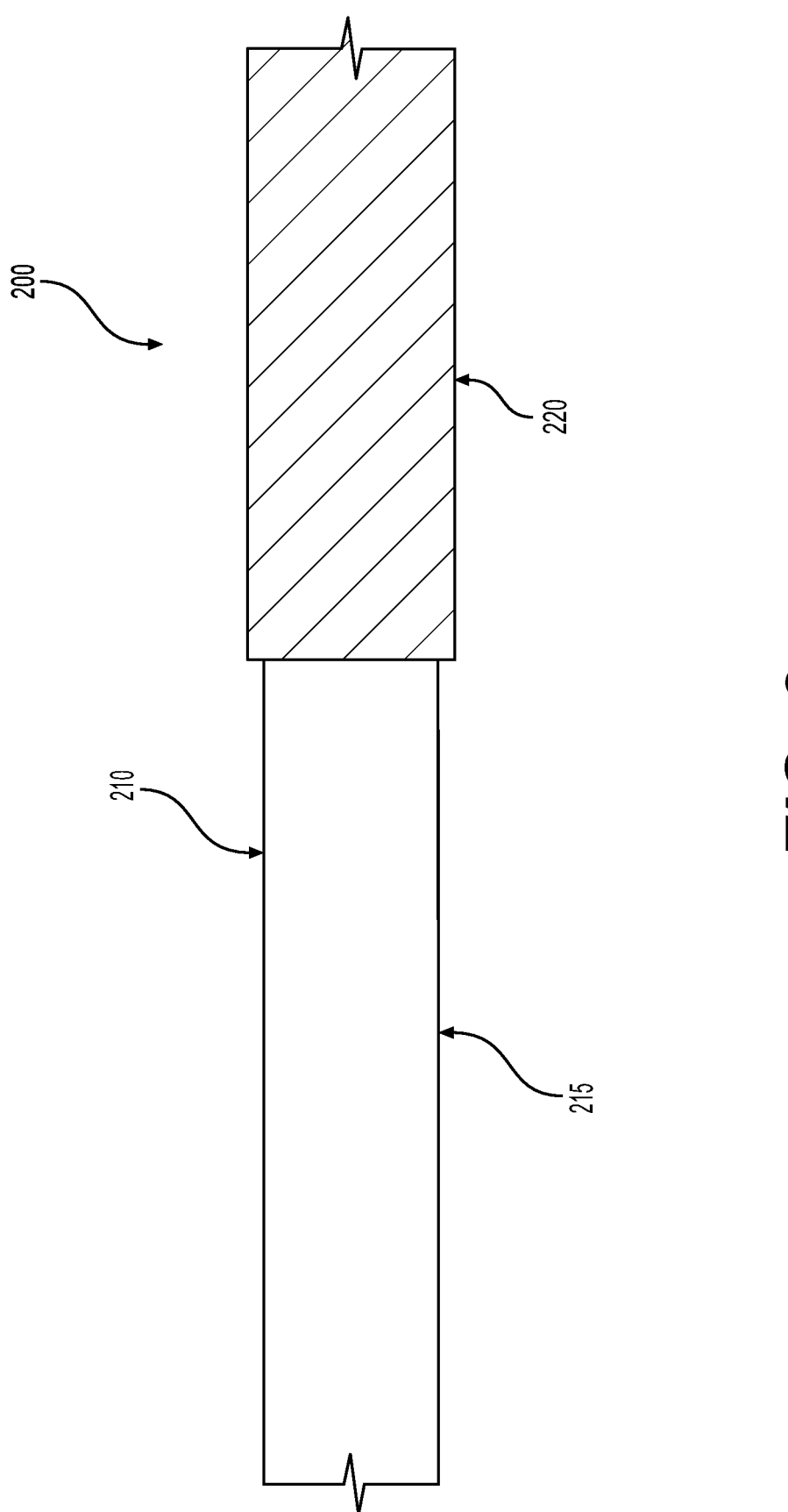
FIG. 2 is a diagram showing a cross-section of a snap band dressing according to one or more aspects of the present disclosure.

Referring now to FIG. 2, a cross-section of a snap band dressing device 200 is shown according to one or more aspects of the present disclosure. The snap band dressing device 200 includes a snap band (e.g., similar or the same as snap band 110 of FIG. 1) having two outer edges 210, 215 (e.g., flexible metal or plastic surfaces) disposed on opposite lateral sides (i.e., the long sides) of a top and bottom face of the snap band. An antimicrobial containing material 220, including any of the aforementioned materials, for example, may be disposed centrally or otherwise offset upon the snap band and dosed with an antimicrobial substance. Accordingly, the antimicrobial containing material 220 may be located centrally upon the snap band, may be positioned at any or both ends of the snap band, along only a portion of a top or bottom face of the snap band, or along the entirety of a face of the snap band, without departing from the scope of the present disclosure. Moreover, it is to be appreciated that while the antimicrobial containing material 220 is shown as a contiguous material extending beyond both outer edges 210, 215, the antimicrobial containing material 220 may be discontiguous and may extend beyond only a single edge 210, 215, extend to meet one or both of the outer edges 210, 215, or fail to extend to or beyond one or both of the edges 210, 215, without departing from the scope of the present disclosure.

Figure 3:
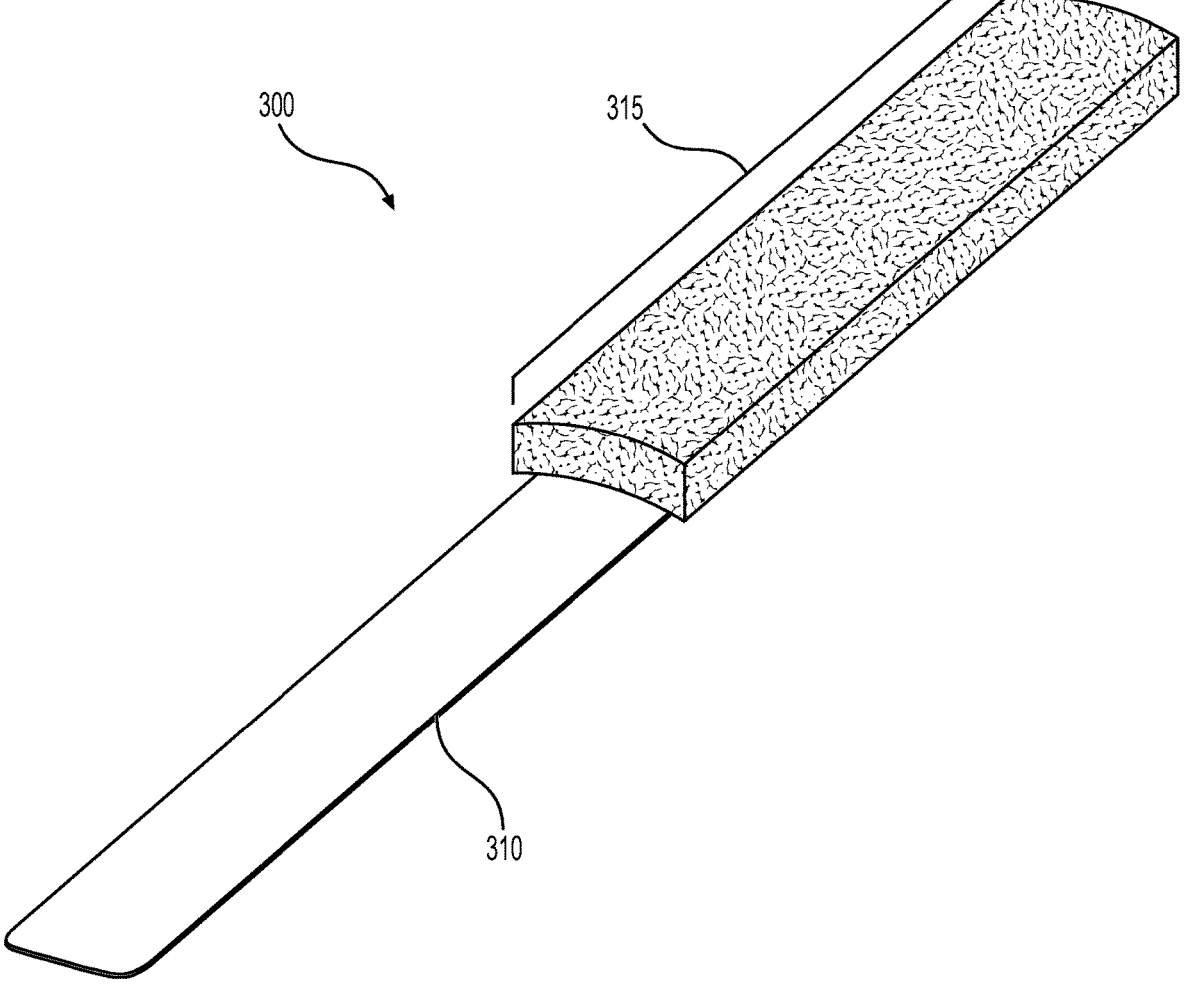
FIG. 3 is a diagram of a snap band dressing device comprising an antimicrobial foam material according to one or more aspects of the present disclosure.
Figure 4:
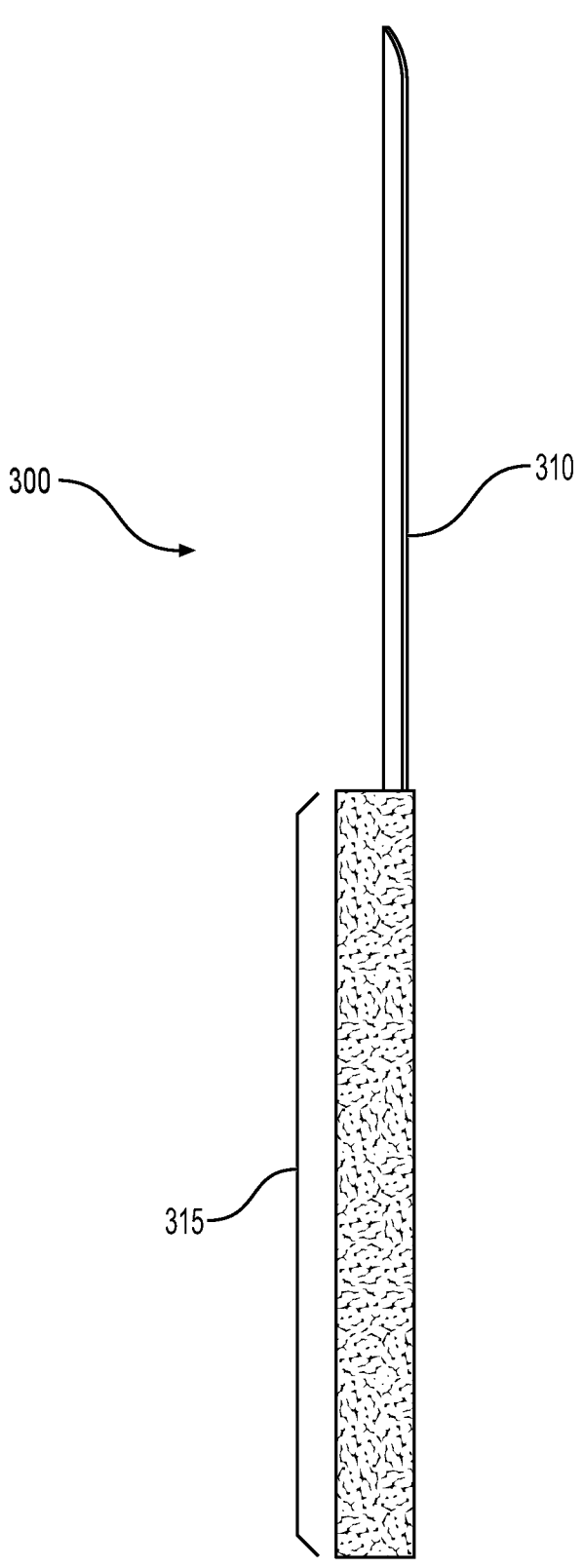
FIG. 4 is a side-view of the snap band dressing device of FIG. 3.

Referring now to FIG. 3, illustrated is a diagram of a snap band dressing device 300 comprising an antimicrobial containing material of foam, according to one or more aspects of the present disclosure. As shown, the snap band dressing device 300 comprises snap band 310 and an antimicrobial containing material 315 of foam adhered to the snap band 310 utilizing one or more biocompatible adhesives. The foam material 315 is relatively thick compared to the thickness of the snap band 310 and thus can hold a sufficient quantity of antimicrobial substance for prolonged use. The particular thickness is not considered to be particularly limiting provided that the snap band dressing device can close around a circumferential wound site (e.g., pin site) without interfering with other elements, such as the frame of an external fixator device. As shown, the foam material 315 extends beyond the edges of the snap band 310 which may provide comfort to the patient at the location of the wound site which the snap band dressing device is protecting, but it is not necessary that this be the case. As provided above, the foam material 315 (or any other antimicrobial containing material) may extend beyond only a single edge or no edges of the snap band 310, be located along the entirety or only a portion at any place along the length of a face of the snap band 310, and may be discontiguous or contiguous, without departing from the scope of the present disclosure. FIG. 4 illustrates a side view of the snap band dressing device 300 of FIG. 3, including the snap band 310 and antimicrobial containing material 315 of foam.

Figure 5:
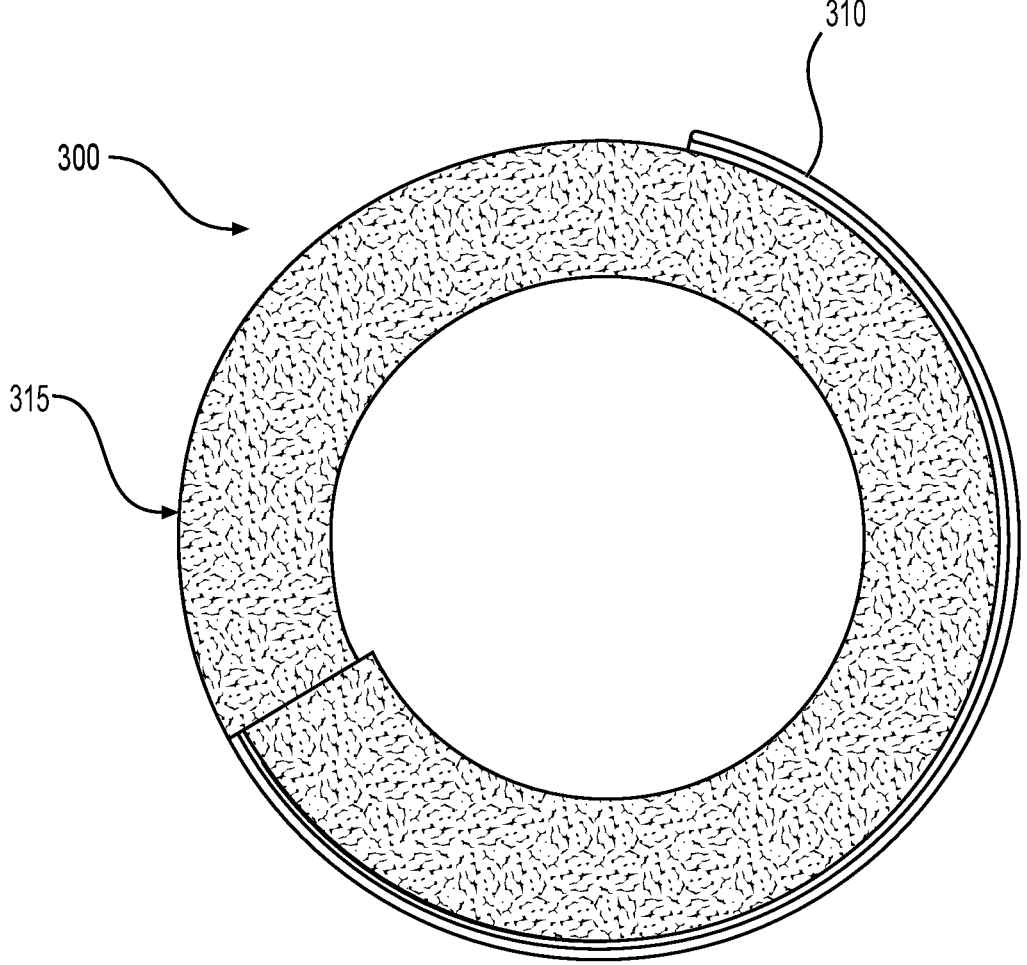
FIG. 5 is a collapsed view of the snap band dressing device of FIG. 3.

Referring now to FIG. 5, illustrated is the collapsed (also described as coiled) structural state of the snap band dressing device 300 of FIG. 3. That is, the bistable spring is engaged in a first configuration in FIGS. 3 and 4 such that the snap band dressing device 300 is in an elongated, open, and relatively flattened configuration and engaged in a second configuration in FIG. 5 (and FIG. 6 discussed below) such that the snap band dressing device 300 is in a collapsed, coiled cylindrical configuration. The change in configurations between the two structural states can be achieved by applying minor manual pressure, thus making the use of the snap band dressing device 300 particularly simple for healthcare professionals and patient use. The snap band 310 coils upon itself thereby causing the antimicrobial containing material 315 to encompass the entire inner circumference of the collapsed snap band dressing device 300 and, accordingly, providing full protection around the circumference of a wound site. Indeed, FIG. 6 illustrates the snap band dressing device 300 in operation.

Figure 6:
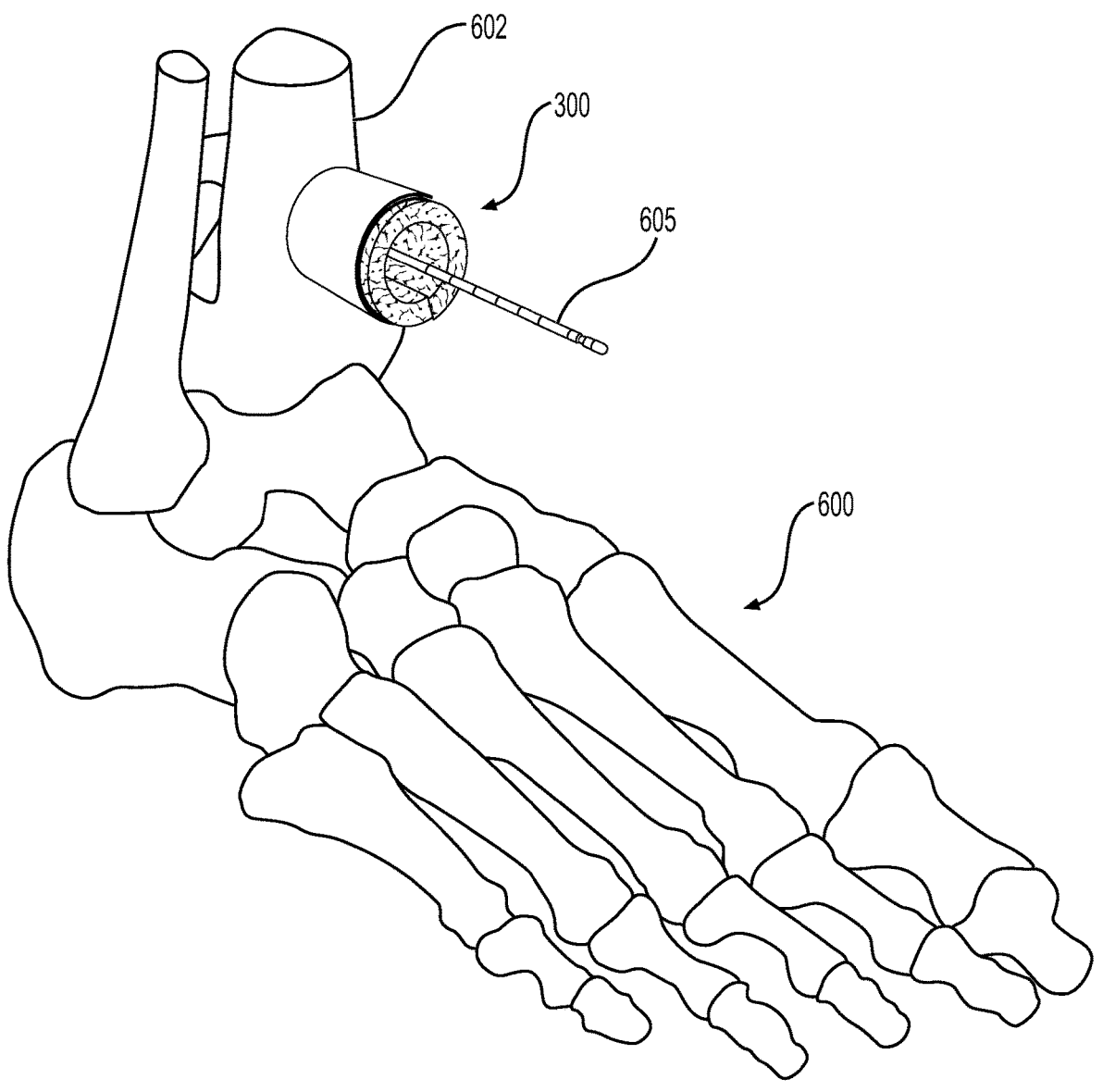
FIG. 6 is a diagram of a collapsed view of the snap band dressing device of FIG. 3 positioned around a circumferential wound site according to one or more aspects of the present disclosure.

Referring to FIG. 6, illustrated is a pin-fixed foot bone 600 showing the collapsed view of the snap band dressing device of FIG. 3, as shown in FIG. 5, positioned around a pin 605, according to one or more aspects of the present disclosure. Representative bone, tibia 602, is pin-fixed to maintain bone fragments in place for healing using pin 605. Abutting the percutaneous pin site location (skin not shown), the snap band pin dressing device 300 is collapsed around the pin 605. Accordingly, the antimicrobial substance contained within the antimicrobial containing material 315 (of FIGS. 3-5) contacts the percutaneous puncture and provides, such as by contact or elution (e.g., seepage over time), for example, antimicrobial protection to the wound site. The snap band pin dressing device 300 further contacts the pin 605 to ensure that the snap band pin dressing device 300 remains securely in place.

In one or more aspects of the present disclosure, a snap band dressing device may include first to third layers. The bottom (first) layer is a flexible slip resistant material configured to lie directly on a circumferential wound site. The second layer is a resilient flexible material that has a width wide arc, and when is in a linear shape, is in an extended condition and is coiled when initiated by the width wide arc (the snap band substrate). The third layer is a foam or sponge-like antimicrobial containing material configured to sit on the edge of the second layer abutting the skin, extending beyond the edge abutting the skin, or extending beyond both edges of the second layer (and thus first layer as well), and further substantially covering the entirety of the second layer. This serves as an all-encompassing, easy to apply dressing over percutaneous circumferential wound sites (e.g., pins for an external fixator). The snap band dressing device described herein eliminates the process of having to individually uncoil dressing materials, submerging the dressing materials in a solution, and further individually coiling each circumferential wound site, all while ensuring the dressing does not loosen or move from the circumferential wound site. By gently slapping the snap band dressing device against the desired circumferential would site or otherwise manually engaging the bistable spring, the flexible material then fully encircles the circumferential wound site circumferentially, decreasing risk of infection, loosening of the dressing, all while providing an evenly distributed antibacterial zone surrounding the skin.

The various aspects of the snap band dressing device described above are illustrative and not intended to be limiting. Further aspects and alternatives may be used in various examples, such as those described herein.

In one or more aspects, a snap band dressing device has a snap band with a bistable spring constructed with a foam, sponge, or other absorbent open cell product edge that serves as the skin interface as well as the side of the product that would be in contact with the circumferential wound site and skin. On the edge of the band that interfaces with the skin, there is a covering directly adhered to the back of a flexible material that would either be dry or contain an antimicrobial substance. The snap band dressing would then coil around the circumferential wound site after being gently snapped or otherwise engaged against the circumferential wound site and mobilized against the skin.

In one or more aspects, a snap band dressing device has a snap band with a bistable spring which itself inherently contains an antimicrobial substance (e.g., an antiseptic and/ or bactericidal solution). Within the band, there is an inner contained cell 130 that is filled with the antimicrobial solution 132 that is connected to the remainder of the band, however, there is a small valve 134 that holds the solution 132 back from saturating the band. The valve 134 responds to slight force to release the fluid 132 into the previously empty container, saturating the foam with the solution 132. In one example, the cell is located in a center interior of foam material. In another example, the cell may be in a bladder located outside the foam material. Applying pressure can release the substance so it elutes into the material and then to the wound site. At this point the band would be gently snapped around the circumferential wound site and mobilized to the skin edge. Add a description about the external and internal reservoirs.

In one or more aspects, a snap band dressing device has a snap band having an outer casing and inner casing. The outer casing may include a bistable spring. The inner casing is relatively fragile compared to the outer casing. The inner casing may be for example, plastic, sugar glass, or other frangible material, which contains an antimicrobial substance. When the snap band is gently struck against a percutaneous wound site (e.g., pin) or otherwise engaged, the fragile casing would break due to the force resulting in the antimicrobial substance being released resulting in the absorbent material taking up the solution. In some examples, the inner casing is within a foam material or other antimicrobial containing material for release therein and elution therefrom upon breaking the frangible casing. Once again, this would be mobilized to the skin edge.

In one or more aspects, a combination of the first three aspects described above with an added component is provided, including a liquid component which would be fluorescent when lights are turned off (separate from the antimicrobial substance). Once the fluorescence is gone from sight then one would know that the snap band needs to be changed; that is, indicating a change in the condition of the snap band dressing device (e.g., depletion of antimicrobial substance).

In one or more aspects, a snap band dressing device has a snap band which may be a combination of acid/base test strip (Litmus paper) with the antimicrobial containing material which would be in contact with the skin interface. One would be able to look at the litmus strip which is in contact with the skin interface, once this indicator changes color due to an acidic or basic environment one would have an idea of the bacterial burden, further individualizing the wound care regimen.

In one or more aspects, a package is provided with bistable spring snap bands separate from the antimicrobial containing material and antimicrobial substance; the antimicrobial containing material need not initially comprise the antimicrobial substance but may include it in other aspects, without departing from the present disclosure. The antimicrobial containing material may be contained within a separator container and an applicator (e.g., foam with connecting bracket) may be integral with the antimicrobial containing material or otherwise separate and used to attach the antimicrobial containing material to the snap band (e.g., snap band substrate). For example, the antimicrobial containing material can be attached to a bracket applicator or other mechanical fastener applicator, such as one shaped like a C, where the opening of the C would be the entry point for the band to slide or clip into, allowing for easy attachment to the band itself. Another variation may have an applicator shaped like a C without a bracket attachment where the band directly slides into the applicator, thereby attaching the antimicrobial containing material. Another variation may be a circumferential applicator with a hole in the middle wide enough to allow the snap band to slide through. Once one is ready to apply the snap band, the antimicrobial containing material is attached via the applicator to the snap band and then snapped into place. This would allow for the snap band to be reused while only the antimicrobial containing material and applicator would need to be replaced. In other instances, the applicator may be reusable if it is not integral to the antimicrobial containing material.

In one or more aspects, a snap band with an antimicrobial containing material is attached to the end of the snap band which would interface with the skin. On the surface of the antimicrobial containing material abutting the skin, an overlying flexible covering impregnated with an antibacterial substance may be provided. The back of the flexible covering may be adhered to the side of the antimicrobial containing material closest to the skin. Overlying the flexible covering may be a minimally adhesive removable strip, similar to what is covering the skin surface of an adhesive bandage. Once one is ready to apply the snap band, the overlying adhesive covering would be removed, exposing the antimicrobial containing material with the flexible covering impregnated with an antibacterial substance for receipt into the antimicrobial containing material may be mobilized to the skin.

In one or more aspects, a snap band has a material replacing the antimicrobial containing material and composed of a material which does not contain an antimicrobial substance but provides antimicrobial protection. This material may be any material comprising antimicrobial properties (e.g., antiseptic properties), but not limited to, gauze, ADAPTIC™ material, XEROFORM™ material.

In one or more aspects, and in addition to any of the above listed aspects alone or in combination, a slip resistant piece may be added to the snap band circumferentially which would be in contact with the (e.g., pin site) itself. An advantage of the slip resistant piece would be to hold the entirety of the snap band dressing device in its position more firmly and decrease the chances that it slips away from the skin edge.

In one or more aspects, the present disclosure solves a problem of wrapping a wound dressing around a circumferential wound site (e.g., pin site) which may be in close proximity to another circumferential wound site. A solution is provided which allows the bistable spring of a snap band to snap itself in opposite directions around a fulcrum at the center. In this way the snap band would snap in opposite directions and form the shape of an infinity sign once in closed form.

In one or more aspects, a strap or tab is added to the end of the snap band. This strap would allow for easy removal of the band when it is secured. By pulling on the strap at the end of the snap band, the snap band may unravel itself and come loose (disrupting the bistable spring into the elongated, open structural state). The tab may be attached to either one or both ends of the snap band. This tab can also be used to adjust the tightness of the snap band; by pulling on the tab slightly it can tighten the strap band against the circumferential wound site and with the addition of an adhesive to the tab it can be secured to the body of the band.

In a one or more aspects, the snap band may act as a place holder for a dressing that is wrapped around the external wound site. The snap band itself would have no antimicrobial containing material or at least not one with loaded antimicrobial substance or an otherwise antimicrobial substance inherent to itself. The snap band would snap around the circumferential wound site and secure a dressing which would already be wrapped around the skin at the circumferential wound site interface.

In a further feature, snap band dressing devices may be combined in a self-contained package. In addition to serving as the dressing component, when in the elongated and open state, the snap band may serve as the top of the package, whereas an absorbent antimicrobial containing material may serve as the bottom and initially lacking an antimicrobial solution. The foam can be placed side down in a container with a shallow compartment that would allow for filling the compartment with an antibacterial/bactericidal solution to allow for the band to be easily saturated prior to application; while the opposite edge would be facing upwards. There may be a covering overlying the edge facing opposite the shallow compartment, for example but not limited to, a wax adhesive that could easily be peeled off revealing the underlying product. Additionally, there would be breakable connections between each snap band allowing for quick removal and application. Once the surrounding material is saturated by the solution, the band can then be gently snapped into place around circumferential wound sites (e.g., external fixator pins) and mobilized to abut the skin, for example.

In this way, the present disclosure provides a unique way to protect a circumferential wound site and elute an antimicrobial fluid which may minimize the microbial (e.g., bacterial) burden and infectious rate while simultaneously maintaining a stable fixation point as a dressing.

Further advantages of snap band dressing devices and methods described herein are quick and easy application compared to the traditional way of cutting material to size, submerging in antimicrobial solution(s), and application around the circumferential wound sites (e.g., pin sites) which can many times come loose. Snap band dressing devices described here are more secure than conventional foam pads applied around circumferential wound sites that are not held on securely. Snap band dressing devices also do not require a process of making a dressing individually for each individual site like some foam pad designs.

As described herein, in various aspects, a snap band dressing device advantageously uses a bistable spring. A snap band dressing device may include a snap band composed of a metal, silicon, or different flexible composite, or coated with a liquid rubber, which when gently snapped against a circumferential wound site would coil around circumferentially. The snap band is configured to exist in two mechanical states, an elongated (opened) and a collapsed (coiled) shape. On the edge of the snap band abutting the skin, there may be an antimicrobial containing material having or capable of receiving an antimicrobial substance when in use. This design makes for quick and easy application which will significantly reduce operating room time and can be applied in a shorter time period versus the traditional method of application, while still providing the necessary stability of the dressing. Once one or more circumferential wound sites need to be changed, this method would once again reduce application time which would increase efficiency and productivity in the ability to see patients with a faster turnover time as well as decrease patient discomfort. Moreover, the ease of use can allow patients to directly change their dressings. Removing the snap band dressing device off of the circumferential wound sites is just as easy as putting it on as one would just pull on the end that is open allowing the band to roll right off or otherwise simply uncoil the snap band dressing device away from the site.

In this way, snap band dressing devices may be a beneficial tool in any dressing regimen for any percutaneous circumferential wound sites, as defined herein, including external fixation as well as an external fixator kits due to ease of use, reduced time of application, and ability to secure itself against the circumferential wound site and to skin interface which would decrease irritation and theoretically decrease risk of site infection. Furthermore, increasing the amount of surface area in touch with the site-skin interface, as well as the surrounding areas, may result in a greater chance of decreasing site infections. In examples, the diameters of sites can range from about 1.6 millimeters (mm) to about 6.5 mm. The design of this product would be able to accommodate for all variations in sizes, including if there are smaller or larger circumferential wound site devices that are not yet utilized.

An additional benefit of this all in one, easy to apply type dressing goes hand in hand with the advancement of telehealth. With an increasing provider and patient population utilizing the technology of virtual health, this device would be an asset with dressing changes that do not take place in the office, as described above. Whether the patient, a family member, or home health be responsible for dressing changes, this process would no longer be left up to individual discretion of how to apply the dressing, but rather a predetermined consistent system.

The present disclosure provides, among others, the following aspects, each of which may be considered as optionally including any alternative thereof.

Aspect 1: A device for dressing one or more circumferential wound sites comprising: a snap band having an elongated open shape and a coiled closed shape; and a layer integral with or coupled to the snap band and configured to elute a fluid to a wound site when the snap band is positioned around a circumferential wound site in the coiled closed shape.

Aspect 2: A device for dressing one or more circumferential wound sites comprising: a snap band having an elongated open shape and a coiled closed shape; and a cell region having an antimicrobial substance within the snap band, wherein the cell region includes a valve configured to elute the antimicrobial substance from the cell region to a wound site when the snap band is positioned around the circumferential wound site in the coiled closed shape.

Aspect 3: A device for dressing one or more circumferential wound sites comprising: a snap band having an elongated open shape and a coiled closed shape; and a casing disposed on an inner surface of the snap band and configured to elute an antimicrobial substance from the casing to a wound site when the snap band is positioned around the circumferential wound site in the coiled closed shape.

Aspect 4: A method for dressing one or more circumferential wound sites comprising: snapping a snap band in a coiled closed shape about a circumferential wound site; and eluting an antimicrobial substance to a wound site when the snap band is positioned around the circumferential wound site in the coiled closed shape. The snap band may further include an antimicrobial layer integral with or coupled to the snap band for eluting the fluid (e.g., antimicrobial substance).

Aspect 5: A package for dressing one or more circumferential wound sites comprising: a snap band having an elongated open shape and a coiled closed shape; a layer couplable to the snap band and configured to elute a fluid to a wound site when the snap band is positioned around the circumferential wound site in the coiled closed shape; and an applicator for coupling the snap band and the layer.

Nonlimiting examples of Aspects 1, 2, and 3 may include one or more of the following elements:

Element 1: Wherein the snap band includes a bistable spring.

Element 2: Wherein the layer is an antimicrobial containing material comprising an antimicrobial substance.

Element 3: Wherein the antimicrobial containing material is one of a foam, a hydrogel, a hydrocolloid, an alginate, and any combination thereof.

Element 4: Wherein the antimicrobial containing material is a foam.

Element 5: Wherein the antimicrobial substance is one of a betadine, an alcohol, a peroxide, a chlorhexidine, acetic acid, silver, an iodine, polyhexamethyl biguanide, sodium hypochlorite, VASHE®, PRONTOSAN®, ADAPTIC™, XEROFORM™, and any combination thereof.

Element 6: Further comprising a slip resistant layer disposed on an inner surface of the snap band.

Element 7: Wherein the snap band comprises two outer edges and the layer is disposed beyond at least one outer edge of the snap band and configured to contact the circumferential wound site when the snap band is positioned around the circumferential wound site in the coiled closed shape.

Element 8: Wherein the snap band comprises two outer edges and the layer is disposed beyond both of the two outer edges of the snap band and configured to contact the circumferential wound site when the snap band is positioned around the circumferential wound site in the coiled closed shape.

Element 9: Further comprising test paper for indicating an acid or base condition.

Element 10: Further comprising a fluorescing liquid for indicating a change of snap band condition.

Element 11: Wherein the circumferential wound site is a percutaneous pin site of an external fixator.

Element 12: Wherein the circumferential wound site is a catheter site.

Non-limiting examples of combinations of Aspect 1 any of the following Elements: 1 and 2; 1 and 3; 1 and 4; 1 and 5; 1 and 6; 1 and 7; 1 and 8; 1 and 9; 1 and 10; 1 and 11; 1 and 12; 2 and 3; 2 and 4; 2 and 5; 2 and 6; 2 and 7; 2 and 8; 2 and 9; 2 and 10; 2 and 11; 3 and 4; 3 and 5; 3 and 6; 3 and 7; 3 and 8; 3 and 9; 3 and 10; 3 and 11; 3 and 12; 4 and 5; 4 and 6; 4 and 7; 4 and 8; 4 and 9; 4 and 10; 4 and 11; 4 and 12; 5 and 6; 5 and 7; 5 and 8; 5 and 9; 5 and 10; 5 and 11; 5 and 12; 6 and 7; 7 and 9; 7 and 10; 7 and 11; 7 and 12; 8 and 9; 8 and 10; 8 and 11; 8 and 12; 9 and 10; 9 and 11; 9 and 12; 10 and 11; 10 and 12; 11 and 12; any of 1-7 and 9-11; any of 1-7, 9, 10, and 12; any of 1-6 and 8-11; any of 1-6, 8-10, and 12; among other combinations.

Non-limiting examples of combinations of Aspect 2 any of the following Elements: 1 and 5, 5 and 6; 5 and 9; 5 and 10; 5 and 11; 5 and 12; 9 and 10; 9 and 11; 9 and 12; 10 and 11; 10 and 12; 11 and 12; any of 5, 6, and 9-11; any of 5, 6, 9, 10, and 12; among other combinations.

Non-limiting examples of combinations of Aspect 3 any of the following Elements: 1 and 5, 5 and 6; 5 and 9; 5 and 10; 5 and 11; 5 and 12; 9 and 10; 9 and 11; 9 and 12; 10 and 11; 10 and 12; 11 and 12; any of 5, 6, and 9-11; any of 5, 6, 9, 10, and 12; among other combinations.

Non-limiting examples of combinations of Aspect 4 any of the following Elements: 1 and 2; 1 and 3; 1 and 4; 1 and 5; 1 and 6; 1 and 7; 1 and 8; 1 and 9; 1 and 10; 1 and 11; 1 and 12; 2 and 3; 2 and 4; 2 and 5; 2 and 6; 2 and 7; 2 and 8; 2 and 9; 2 and 10; 2 and 11; 3 and 4; 3 and 5; 3 and 6; 3 and 7; 3 and 8; 3 and 9; 3 and 10; 3 and 11; 3 and 12; 4 and 5; 4 and 6; 4 and 7; 4 and 8; 4 and 9; 4 and 10; 4 and 11; 4 and 12; 5 and 6; 5 and 7; 5 and 8; 5 and 9; 5 and 10; 5 and 11; 5 and 12; 6 and 7; 7 and 9; 7 and 10; 7 and 11; 7 and 12; 8 and 9; 8 and 10; 8 and 11; 8 and 12; 9 and 10; 9 and 11; 9 and 12; 10 and 11; 10 and 12; 11 and 12; any of 1-7 and 9-11; any of 1-7, 9, 10, and 12; any of 1-6 and 8-11; any of 1-6, 8-10, and 12; among other combinations.

Non-limiting examples of combinations of Aspect 5 any of the following Elements: 1 and 2; 1 and 3; 1 and 4; 1 and 5; 1 and 6; 1 and 7; 1 and 8; 1 and 9; 1 and 10; 1 and 11; 1 and 12; 2 and 3; 2 and 4; 2 and 5; 2 and 6; 2 and 7; 2 and 8; 2 and 9; 2 and 10; 2 and 11; 3 and 4; 3 and 5; 3 and 6; 3 and 7; 3 and 8; 3 and 9; 3 and 10; 3 and 11; 3 and 12; 4 and 5; 4 and 6; 4 and 7; 4 and 8; 4 and 9; 4 and 10; 4 and 11; 4 and 12; 5 and 6; 5 and 7; 5 and 8; 5 and 9; 5 and 10; 5 and 11; 5 and 12; 6 and 7; 7 and 9; 7 and 10; 7 and 11; 7 and 12; 8 and 9; 8 and 10; 8 and 11; 8 and 12; 9 and 10; 9 and 11; 9 and 12; 10 and 11; 10 and 12; 11 and 12; any of 1-7 and 9-11; any of 1-7, 9, 10, and 12; any of 1-6 and 8-11; any of 1-6, 8-10, and 12; among other combinations.

One or more illustrative incarnations incorporating one or more invention elements are presented herein. Not all features of a physical implementation are described or shown in this application for the sake of clarity. It is understood that in the development of a physical embodiment incorporating one or more elements of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While various aspects are described herein in terms of "comprising" various components, the aspects can also "consist essentially of" or "consist of" the various components.

Many alterations, modifications, and variations will be apparent to those skilled in the art in light of the foregoing description without departing from the spirit or scope of the present disclosure.

Therefore, the present disclosure is well adapted to attain the ends and advantages mentioned as well as those that are inherent therein. The particular examples and configurations disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative examples disclosed above may be altered, combined, or modified and all such variations are considered within the scope and spirit of the present disclosure. The embodiments illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

What is claimed is:

1. A device, comprising:
a snap band having an antimicrobial material, wherein the snap band is configured to transition between an elongated open shape and a coiled closed shape, and wherein the snap band is configured to transition from the elongated open shape to the coiled closed shape to wrap around an object extending from a wound site of a patient; and
a cell region disposed within an interior of the antimicrobial material, the cell region having an antimicrobial substance and a valve, wherein the valve is configured to release the antimicrobial substance into the antimicrobial material based on a force being applied to the valve, and wherein antimicrobial material including the antimicrobial substance is configured to elute the antimicrobial substance to a the wound site when the snap band is in the coiled closed shape around the object.

2. The device of claim 1, wherein the snap band includes a bistable spring.

3. The device of claim 1, wherein the antimicrobial material is one of a foam, a hydrogel, a hydrocolloid, an alginate, and any combination thereof.

4. The device of claim 1, further comprising a slip resistant layer disposed on an inner surface of the snap band.

5. The device of claim 1, wherein the object is a percutaneous pin of an external fixator.

6. The device of claim 1, wherein the object is a catheter.

7. The device of claim 1, further comprising test paper for indicating an acid or base condition.

8. The device of claim 1, further comprising a fluorescing liquid for indicating a change of snap band condition.

9. The device of claim 1, wherein only the layer edge of the layer is configured to contact the wound site when the snap band is in the coiled closed shape around the object.

10. The device of claim 1, wherein the snap band includes a snap band edge and the layer includes a layer edge that extends beyond the snap band edge, and wherein only the layer edge of the layer is configured to contact the wound site when the snap band is in the coiled closed shape around the object.

\* \* \* \* \*